United States Patent
Ryu et al.

(10) Patent No.: US 11,607,561 B2
(45) Date of Patent: Mar. 21, 2023

(54) METHOD FOR MEASURING CONCENTRATION DISTRIBUTION OF BORON FOR BNCT USING MRI, AND TREATMENT PLANNING METHOD FOR BNCT

(71) Applicants: GACHON UNIVERSITY OF INDUSTRY-ACADEMIC COOPERATION FOUNDATION, Seongnam-si (KR); GIL MEDICAL CENTER, Incheon (KR)

(72) Inventors: Yeun Chul Ryu, Suwon-si (KR); Jun-Young Chung, Incheon (KR); Sang-Yoon Lee, Incheon (KR); Tatsuo Ido, Incheon (KR); Kyoung-Nam Kim, Incheon (KR); Ye Ji Han, Seoul (KR)

(*) Notice: Subject to any disclaimer, the term of this patent is extended or adjusted under 35 U.S.C. 154(b) by 1065 days.

(21) Appl. No.: 16/304,649

(22) PCT Filed: Oct. 31, 2017

(86) PCT No.: PCT/KR2017/012193
§ 371 (c)(1),
(2) Date: Nov. 26, 2018

(87) PCT Pub. No.: WO2018/080290
PCT Pub. Date: May 3, 2018

(65) Prior Publication Data
US 2019/0282833 A1    Sep. 19, 2019

(30) Foreign Application Priority Data

Oct. 31, 2016 (KR) .................. 10-2016-0143640

(51) Int. Cl.
*A61N 5/10* (2006.01)
*A61B 5/055* (2006.01)

(52) U.S. Cl.
CPC ............ *A61N 5/1039* (2013.01); *A61B 5/055* (2013.01); *A61N 5/103* (2013.01); *A61N 2005/109* (2013.01); *A61N 2005/1055* (2013.01)

(58) Field of Classification Search
CPC .... A61N 5/1039; A61N 5/103; A61N 5/1031; A61N 2005/1055; A61N 2005/109; A61B 5/055; A61B 5/0036
See application file for complete search history.

(56) References Cited

U.S. PATENT DOCUMENTS

2016/0158391 A1* 6/2016 Blaha ................. A61K 51/0491
                                                                          424/1.65
2018/0318420 A1* 11/2018 Takeyoshi ............ A61N 5/1077

FOREIGN PATENT DOCUMENTS

EP    1658878 A1 *  5/2006 ........... A61N 5/1039
EP    1658878 A1     5/2006
(Continued)

OTHER PUBLICATIONS

Shibata, Y. A. S. U. S. H. I., et al. "Prediction of boron concentrations in blood from patients on boron neutron capture therapy." Anticancer research 23.6 (2003): 5231-5236. (Year: 2003).*
(Continued)

*Primary Examiner* — Sean D Mattson

(57) ABSTRACT

Disclosed are a method of measuring concentration distribution of boron for boron neutron capture therapy (BNCT) using magnetic resonance imaging (MRI) alone and a treatment planning method for BNCT. The methods include (a) acquiring an anatomical image of a patient and measuring a boron concentration from magnetic resonance (MR) data, (b) extracting a boron concentration change prediction parameter of the patient and predicting the concentration over time, (c) calculating and verifying a boron distribution (Continued)

prediction value estimated by boron imaging and spectral analysis, and (d) deriving an optimal time for BNCT based on the verified results.

5 Claims, 1 Drawing Sheet

(56) References Cited

FOREIGN PATENT DOCUMENTS

| JP | 2004-337268 A | 12/2004 |
|---|---|---|
| JP | 2016-112143 A | 6/2016 |
| JP | 2016-159107 A | 9/2016 |
| JP | 2016-214760 A | 12/2016 |

OTHER PUBLICATIONS

Timonen, Marjut, et al. "1H MRS studies in the Finnish boron neutron capture therapy project: Detection of 10B-carrier, Ip-boronophenylalanine-fructose." European journal of radiology 56.2 (2005): 154-159. (Year: 2005).*

Kabalka, George W., Chao Tang, and Peter Bendel. "The role of boron MRI in boron neutron capture therapy." Journal of neuro-oncology 33.1 (1997): 153-161. (Year: 1997).*

Savolainen, Sauli, et al. "Boron neutron capture therapy (BNCT) in Finland: Technological and physical prospects after20 years of experiences." Physica Medica 29.3 (2013): 233-248. (Year: 2013).*

Barth, Rolf F., et al. "Current status of boron neutron capture therapy of high grade gliomas and recurrent head and neck cancer." Radiation Oncology 7.1 (2012): 1-21. (Year: 2012).*

Porcari, P., et al. "In vivo 19F MR imaging and spectroscopy for the BNCT optimization." Applied Radiation and Isotopes 67.7-8 (2009): S365-S368. (Year: 2009).*

Rolf F. Barth et al., "Current status of boron neutron capture therapy of high grade gliomas and recurrent head and neck cancer", Radiation Oncology, 2012, pp. 1-21, vol. 7, No. 146.

* cited by examiner

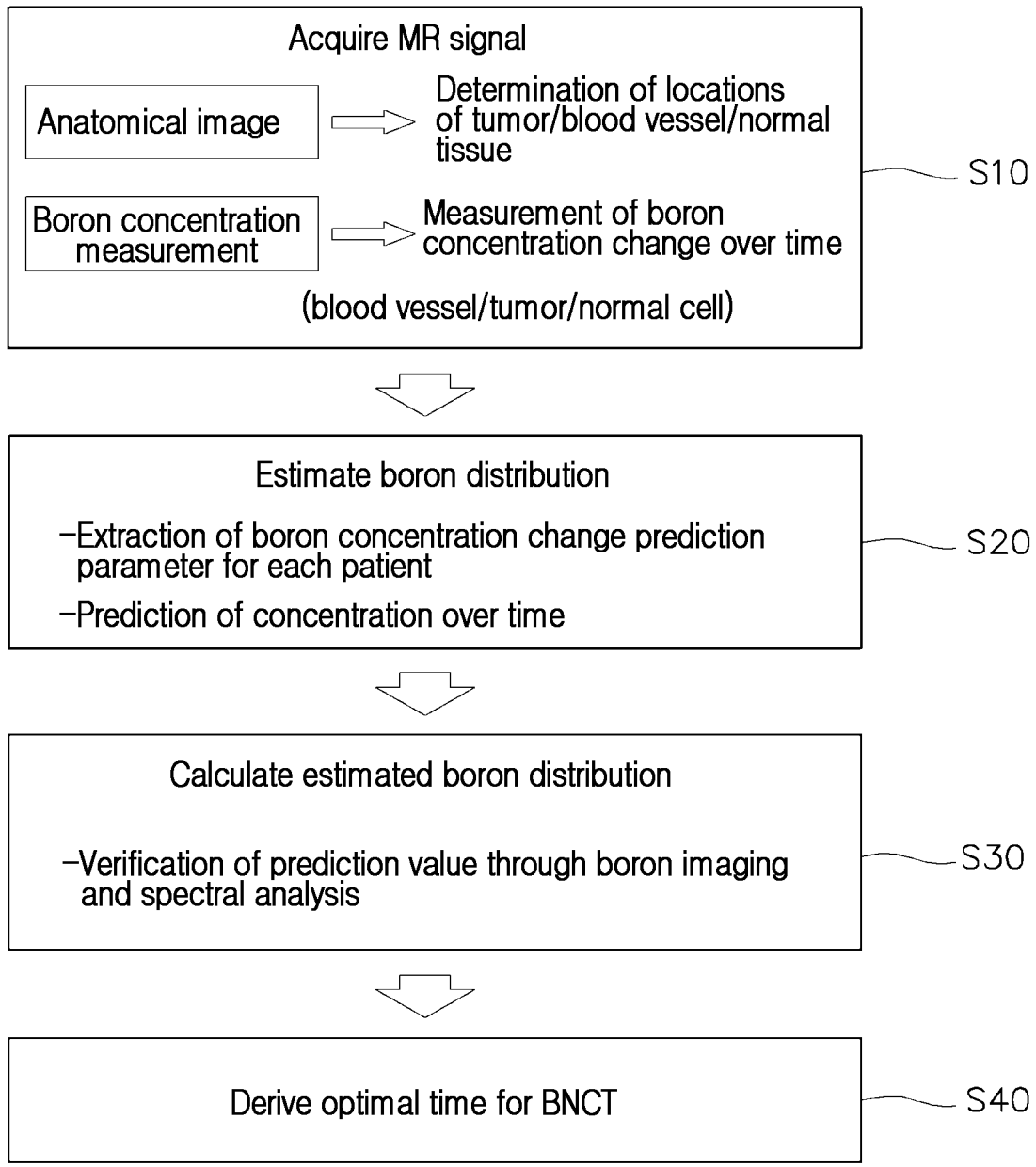

METHOD FOR MEASURING CONCENTRATION DISTRIBUTION OF BORON FOR BNCT USING MRI, AND TREATMENT PLANNING METHOD FOR BNCT

TECHNICAL FIELD

The present invention relates to a method of measuring concentration distribution of boron for boron neutron capture therapy (hereinafter, abbreviated to "BNCT") using magnetic resonance imaging (MRI) alone, and to a treatment planning method for BNCT.

BACKGROUND ART

BNCT is a biochemically targeted radiation therapy based on the nuclear capture and fission reactions that occur when non-radioactive $^{10}B$, which is present as a stable natural isotope, is irradiated with low-energy (0.025 eV) thermal neutrons, and such nuclear reactions generate high linear energy transfer alpha particles ($^{4}He$) and recoiling lithium ($^{7}Li$).

BNCT, using the above properties, is characterized in that a boron drug, which collects only in cancer cells, is administered and then the affected part is irradiated with neutrons, whereby nuclear fission of boron occurs due to the irradiated neutrons, thus generating radiation that destroys only cancer cells. The radiation thus generated is known to be diffused only at the cellular level and not to damage normal cells, resulting in fewer side effects.

Accordingly, BNCT is receiving much attention as a cancer treatment method that may replace a conventional radiation therapy that damages the surrounding normal cells.

For effective BNCT, it is very important to selectively transfer a sufficient amount of boron to all cancer cells.

Also, the treatment plan for BNCT is quite different and is very complex compared to conventional radiation therapy and thus requires special software. As such, the treatment plan is developed using a model made specifically for the treatment target based on CT or MR images, and the radiation dose to be applied to a patient is determined using the parameters thus determined.

Meanwhile, a limiting dose should be determined together with a maximum dose that may be applied to cancer cells without affecting normal cells. This is because accurate information about the micro-distribution of boron in cancer cells and normal cells cannot be known.

In actual BNCT, the fission in the boron capture reaction ($\alpha$, $^{7}Li$) may be characterized by linear energy transfer (LET), and the diffusion distance thereof is very short (approximately 10 μm in average cell size). It is therefore necessary to accurately define the boron distribution at the cellular or subcellular level.

CT or MRI has been used as auxiliary means in conventional treatment planning for BNCT, but is limited to means for identifying the precise high-resolution anatomical structure of a patient. Furthermore, PET or SPECT may be used to measure the concentration of boron, but PET or SPECT provides only a resolution in the centimeter range, and is incapable of obtaining cell-level resolution.

Meanwhile, in order to measure the intracellular residual concentration of boron, a monitoring technique using a blood sample may be employed, but is able to measure only the concentration of boron in the blood, and furthermore, the concentration distribution in cancer tissues and normal tissues, which is regarded as important in actual treatment, cannot be simultaneously measured, making it difficult to maximize the therapeutic effect. Moreover, although the use of a blood sample is meaningful for injection through blood vessels upon in-vivo introduction of boron, when using methods other than injection, such as oral administration, existing results of boron concentration in the blood and boron concentration in tumors cannot be utilized, thus making it difficult to accurately predict the boron concentration.

CITATION LIST

Non-Patent Literature

Rolf F Barth, M Graca H Vicente, Otto K Harling, W S Kiger III, Kent J Riley, Peter J Binns, Franz M Wagner, Minoru Suzuki, Teruhito Aihara, Itsuro Kato and Shinji Kawabata; Current status of boron neutron capture therapy of high grade gliomas and recurrent head and neck cancer; Radiation Oncology 2012 7:146 (www.ro-journal.com/content/7/1/146)

DISCLOSURE

Technical Problem

The present invention has been made keeping in mind the problems encountered in the related art, and the present invention is intended to provide a method of measuring the boron concentration distribution for BNCT, which is capable of acquiring an anatomical information of a patient and accurately measuring a boron concentration using MRI (Magnetic Resonance Imaging) alone, and a treatment planning method for BNCT.

Technical Solution

The present invention provides a treatment planning method for BNCT, comprising: (a) acquiring an anatomical information of a patient and measuring a boron concentration from magnetic resonance (MR) data; (b) extracting a boron concentration change prediction parameter of the patient and predicting the concentration over time; (c) calculating and verifying a boron distribution prediction value estimated by boron imaging and spectral analysis (S30); and (d) deriving an optimal time for BNCT based on the verified results.

Preferably, in step (a), the boron concentration is measured through magnetic resonance spectroscopy and imaging of boron.

Preferably, in step (b), when the time-dependent changes in boron concentration are measured using magnetic resonance spectroscopy and imaging of boron, the boron concentration is measured at least four times for 1 hr or more.

In addition, the present invention provides a method of measuring boron concentration distribution for BNCT, comprising acquiring an anatomical image of a patient and measuring a boron concentration from MR data, and preferably the boron concentration is measured using magnetic resonance spectroscopy and imaging of boron.

Advantageous Effects

According to the present invention, a method of measuring boron concentration distribution for BNCT and a treatment planning method for BNCT can acquire the anatomical information at high resolution and accurately measure the concentration distribution of boron using magnetic resonance (MR) alone, and can also maximize the therapeutic safety and the therapeutic effect.

DESCRIPTION OF DRAWING

FIG. 1 is a flowchart showing a treatment planning process for BNCT according to the present invention.

BEST MODE

The specific structure or functional description presented in the embodiments of the present invention is merely exemplified for the purpose of describing embodiments according to the concept of the present invention, and the embodiments according to the concept of the present invention may be embodied in various forms. Also, the present invention should not be construed as limited to the embodiments set forth herein, but should be understood to include all modifications, equivalents, and alternatives falling within the spirit and scope of the present invention.

Hereinafter, a detailed description will be given of embodiments of the present invention with reference to the appended drawing.

FIG. 1 is a flowchart showing the treatment planning process for BNCT according to the present invention.

With reference to FIG. 1, the treatment planning method for BNCT according to the present invention includes (a) acquiring an anatomical image of a patient and measuring a boron concentration from magnetic resonance (MR) data (S10), (b) extracting a boron concentration change prediction parameter of the patient and predicting the concentration over time (S20), (c) calculating and verifying the boron distribution prediction value estimated by boron imaging and spectral analysis (S30), and (d) deriving the optimal time for BNCT based on the verified results (S40).

In step (a) (S10), MR data is acquired and used to measure the boron concentration as well as the anatomical image, and the anatomical image is acquired through SE (Spin Echo), GE (Gradient Echo) or an imaging technique using the same, which may determine the locations of tumors, normal tissue or blood vessels based on T1 and T2 images of protons that are typically clinically used. Also, the boron concentration is measured based on the MR data, and preferably, the absolute and relative concentration distributions of boron are acquired using 3D techniques not only through MRI but also through magnetic resonance spectroscopy (MRSI/MRS), and the acquired data is combined with proton signal data to determine the concentration distribution of boron in tumor tissues, blood vessels and normal tissues. For the absolute numerical measurement of the boron concentration, a reference material for determining the boron concentration value may be placed around the patient, and may then be used to calibrate the data obtained from the patient. Step (a) is usually performed immediately after completion of boron injection, but the injection of boron may be performed even during acquisition of MRI data for the patient, and in order to obtain data predicting the boron concentration over time, information on how boron is injected should be reflected in the prediction simulation.

In step (b) (S20), changes in boron concentration are tracked. Starting from the time of boron injection, data on changes in the boron concentration in tumors, blood vessels, and normal tissue of the patient is acquired, and damping parameters are extracted using the boron concentration change table observed for each patient, and the concentration over time is predicted. The changes in boron concentration are measured through MRSI/MRS and the values thus measured are used as values representing time-dependent changes in the relative and absolute concentration values of the boron concentration. The prediction parameter is extracted, the concentration over time is predicted, and multiple signals for each patient are measured to thus show the time-dependent changes in boron concentration. Here, the boron concentration change graph may refer to graphs disclosed in the literature of the related art, but may be created through simulation using software in consideration of the biological, chemical, and biophysical phenomena of the boron compound in the patient.

In step (c) (S30), the boron distribution prediction value estimated by boron imaging and spectral analysis is calculated and verified. Here, if there is a difference between the boron concentration value predicted at a specific time and the actual boron concentration value after a certain time in the human body, the prediction parameters are corrected. When this difference falls within a predetermined error range, this indicates that the predicted parameter is an appropriate value. Thus, the initially predicted concentration distribution change parameters may be used unchanged.

In step (d) (S40), the optimal time for BNCT is derived based on the verified results. The derived optimal time is used as a parameter to determine the irradiation time of neutrons after patient transport and boron injection for use in treatment using BNCT.

The treatment planning method for BNCT including the series of steps has the advantage of being able to apply the graph of the time-dependent changes in the boron concentration distribution for each patient. In particular, BNCT is carried out when the boron distribution ratio in tumor cells and blood vessels (or normal cells), which plays a very important role in BNCT efficiency, is maximized, thereby maximizing the therapeutic safety and the therapeutic effect.

Although the embodiments of the present invention have been disclosed for illustrative purposes through the appended drawing, those skilled in the art will appreciate that various modifications, additions and substitutions are possible, without departing from the scope and spirit of the invention as disclosed in the accompanying claims.

What is claimed is:

1. A treatment planning method for BNCT (Boron Neutron Capture Therapy) using MRI (Magnetic Resonance Imaging), comprising steps of:
   (a) acquiring an anatomical image defining locations of tumor tissues and normal tissues of a patient and measuring a boron concentration in the tumor tissues and the normal tissues of the patient based on at least magnetic resonance (MR) data acquired for the patient and combining the acquired anatomical image and the measured boron concentration to determine a concentration distribution of boron in the tumor tissues and the normal tissues;
   (b) measuring time-dependent changes in the boron concentration in the tumor tissues and the normal tissues of the patient to determine a boron concentration change prediction parameter and predicting a boron concentration over time in the tumor tissues and the normal tissues of the patient based on the determined boron concentration change prediction parameter;
   (c) determining whether the predicted boron concentration over time for the patient is within a predetermined error range from an actual boron concentration measured in the patient and using the boron concentration change prediction parameter unchanged in response to determining that the predicted boron concentration over time is within the predetermined error range, while correcting the boron concentration change prediction parameter otherwise; and (d) deriving an optimal time for BNCT based on the boron concentration change prediction parameter as a result of step (c) and performing BNCT on the patient based on the optimal time.

2. The treatment planning method for BNCT of claim 1, wherein in step (a), the boron concentration is measured through magnetic resonance spectroscopy of boron.

3. The treatment planning method for BNCT of claim 1, wherein in step (b), when the time-dependent changes in the boron concentration are measured using magnetic resonance spectroscopy of boron, the boron concentration is measured at least four times for 1 hr or more.

4. The treatment planning method for BNCT of claim 1, wherein the optimal time for BNCT is when the boron distribution ratio in the tumor tissues is maximized.

5. The method of claim 4, wherein the time-dependent changes in the boron concentration are measured using magnetic resonance spectroscopy.

\* \* \* \* \*